(12) United States Patent
Baid

(10) Patent No.: US 10,905,857 B2
(45) Date of Patent: Feb. 2, 2021

(54) INTRAVENOUS CATHETER APPARATUS

(71) Applicant: Poly Medicure Limited, Haryana (IN)

(72) Inventor: Rishi Baid, New Delhi (IN)

(*) Notice: Subject to any disclaimer, the term of this patent is extended or adjusted under 35 U.S.C. 154(b) by 0 days.

(21) Appl. No.: 15/729,972

(22) Filed: Oct. 11, 2017

(65) Prior Publication Data

US 2018/0071494 A1 Mar. 15, 2018

Related U.S. Application Data

(63) Continuation of application No. 14/356,998, filed as application No. PCT/IB2012/051457 on Mar. 27, 2012, now Pat. No. 10,265,508.

(30) Foreign Application Priority Data

Nov. 8, 2011 (IN) .......................... 3159/DEL/2011

(51) Int. Cl.
*A61M 25/06* (2006.01)
*A61M 5/32* (2006.01)

(52) U.S. Cl.
CPC ........ *A61M 25/0618* (2013.01); *A61M 5/329* (2013.01); *A61M 25/0606* (2013.01); *A61M 5/3273* (2013.01); *F04C 2270/0421* (2013.01)

(58) Field of Classification Search
CPC ................ A61M 5/3273; A61M 5/329; A61M 25/0606; A61M 25/0612; A61M 25/0618
See application file for complete search history.

(56) References Cited

U.S. PATENT DOCUMENTS

| 7,604,616 B2* | 10/2009 | Thoresen | A61M 5/3273 604/164.08 |
|---|---|---|---|
| 2005/0277879 A1* | 12/2005 | Daga | A61M 25/0606 604/110 |
| 2010/0222749 A1* | 9/2010 | Baid | A61M 5/3273 604/263 |
| 2010/0241087 A1 | 9/2010 | Moulton | |

FOREIGN PATENT DOCUMENTS

| EP | 2016963 | 1/2009 |
|---|---|---|
| WO | 2009116080 | 9/2009 |
| WO | 2011036574 | 3/2011 |

* cited by examiner

*Primary Examiner* — Manuel A Mendez
*Assistant Examiner* — Justin L Zamory
(74) *Attorney, Agent, or Firm* — Krieg De Vault, LLP; Daniel Tychonievich

(57) ABSTRACT

The invention relates to an intravenous catheter apparatus comprising a catheter hub arranged at a proximal end of a catheter tube, the catheter hub having an inner surface defining a chamber; a needle having a needle tip at its distal end and extending through the chamber and the catheter tube when in a ready position; and a needle guard slidably arranged on the needle and received in the chamber when the needle is in its ready position, wherein the needle guard is configured to guard the needle tip upon withdrawal of the needle from the catheter hub.

9 Claims, 5 Drawing Sheets

INTRAVENOUS CATHETER APPARATUS

CROSS-REFERENCE TO RELATED APPLICATIONS

This patent application is a continuation of, and claims priority to, co-pending U.S. patent application Ser. No. 14/356,998, filed on May 8, 2014, which was a national stage of International Patent Application Serial No. PCT/IB2012/051457, filed on Mar. 27, 2012.

TECHNICAL FIELD

The invention relates to an intravenous catheter apparatus comprising a catheter hub arranged at a proximal end of a catheter tube and having an inner surface defining a chamber; a needle having a needle tip and extending through the chamber and the catheter tube when in a ready position; and a needle guard slidably arranged on the needle and received in the chamber when the needle is in its ready position, wherein the needle guard is configured to guard the needle tip upon withdrawal of the needle from the catheter hub.

BACKGROUND

An intravenous catheter apparatus of this kind is generally known. The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

SUMMARY

It is an object of the present invention to provide an intravenous catheter apparatus which provides better protection against accidental pricking by the needle tip and which is inexpensive to manufacture at the same time.

The object is satisfied by an intravenous catheter apparatus in accordance with claim 1.

The intravenous catheter apparatus of the invention comprises a catheter hub arranged at a proximal end of a catheter tube and having an inner surface defining a chamber; a needle defining an axial direction and having a needle tip, wherein the needle extends through the chamber and the catheter tube when in a ready position; a needle guard slidably arranged on the needle and received in the chamber when the needle is in its ready position, the needle guard including a base portion and first and second arms extending from the base portion, wherein the first arm is deflected radially outwards by the needle against a restoring force when the needle is in its ready position whereby the needle guard is brought into retaining contact with the catheter hub; and retaining means for retaining the needle guard in the chamber as long as the first arm is in its deflected state. The retaining means include a first disc-like retaining protrusion provided on the first arm and a retaining depression formed in the inner surface of the catheter hub and adapted to receive the retaining protrusion.

The disc-like retaining protrusion has the benefit that it is engagement along a circular contact surface with the corresponding retaining depression formed in the inner surface of the catheter hub. Differing from IV catheter apparatuses as known from the prior art, this provides an engagement between the needle guard and the catheter hub along a substantial annular portion of the retaining protrusion and the retaining depression which provides a safe and reliable engagement between the two components as long as the needle guard is in its ready position and is to be prevented from being retracted out of the needle hub. Even if the needle guard is rotated within the catheter hub, this secure engagement between the catheter hub and the needle guard holds the needle guard safely within the catheter hub.

Because of a depression being formed in the inner surface of the catheter hub for retaining the needle guard in the chamber, instead of e.g. a protrusion, the catheter hub can be manufactured more easily and, thus, at less manufacturing cost, in particular if the catheter hub is a plastic part and e.g. formed by injection molding. At the same time the particular design of the first retaining protrusion provided on the needle guard ensures effective engagement of the retaining protrusion with the retaining depression and, thus, reliable retaining of the needle guard in the catheter hub. Hence, the risk of premature release of the needle guard from the catheter hub during withdrawal of the needle from the catheter hub and, thus, the risk of accidental pricking by the needle is reduced.

According to a preferred embodiment, the retaining protrusion is of part-circular, in particular semi-circular shape. More specifically, the retaining protrusion may have generally parallel proximal and distal faces and/or a convex, in particular part-cylindrical, peripheral surface.

According to another embodiment, the first retaining protrusion is arranged in the region of a distal end of the first arm.

According to yet another embodiment, a second disk-like retaining protrusion is arranged on the second arm and adapted to engage with the retaining depression as long as the first arm is in its deflected state.

According to yet another embodiment, the second arm can be deflected along its entire length radially inwards when the needle tip is received between the arms, to thereby allow the second retaining protrusion to disengage from the retaining depression.

According to yet another embodiment, the second retaining protrusion is arranged in the region of a distal end of the second arm. In particular, the second retaining protrusion may be arranged opposite from the first retaining protrusion.

According to yet another embodiment, the retaining depression is an at least part-annular depression, preferably an annular depression.

According to yet another embodiment, the restoring force is created by at least one of an elastic property of the first arm and an additional tension element. For example, the needle guard may comprise a tension element at least partly surrounding the arms in a region proximal of the first retaining protrusion or—instead of surrounding the two arms—biasing the two arms by a linear biasing action. Alternatively or additionally, the first and second arms can be made of a resilient material.

According to yet another embodiment, the first and second arms are made of a plastic material. Preferably, the first and second arms are integrally formed with the base portion also made of a plastic material, e.g. by injection molding.

According to yet another embodiment, the needle comprises an engagement means provided at a distance from the needle tip for engaging with the needle guard and preventing the needle guard from sliding off the needle. Preferably, the engagement means is formed of by enlargement of the radial dimension of the needle in at least one direction as compared with a principal profile of the needle. The engagement means can be found by a local crimp, a shoulder, a bulge formed as an annular widening etc.

According to yet another embodiment, the needle guard comprises a stopping element engaging with the engagement means of the needle when the needle tip is received between the first and second arms. Preferably, the stopping element defines an axial bore having a cross-section adapted to the principal profile of the needle but being smaller than the enlargement of the needle. Furthermore, the stopping element may be made of a material different from the material of the base portion, in particular of a metal material. The stopping element may be of disc-like shape or tubular shape and/or arranged on a distal side of the base portion. It can be fixed in the base portion or supported in a floating manner on the needle.

BRIEF DESCRIPTION OF THE DRAWINGS

A preferred embodiment of the invention will now be described by way of example only with reference to the accompanying drawings.

DETAILED DESCRIPTION

Figure 1:
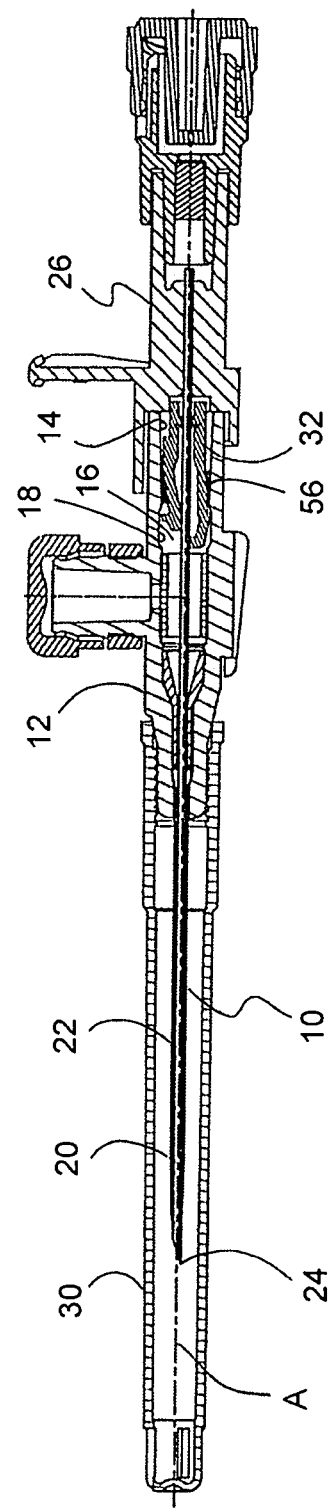
FIG. 1 is a longitudinal sectional view of an intravenous catheter apparatus of the invention.

FIG. 1 shows an intravenous catheter apparatus comprising a catheter tube 10 and a catheter hub 12 attached to the catheter tube 10 at a proximal end thereof. It will be appreciated that the term 'proximal' refers to a position or orientation close to a person handling the intravenous catheter apparatus whereas the term 'distal' refers to a position or orientation distant from this person, wherein the longitudinal direction A of a needle 20 is the reference direction.

The catheter hub 12 has an inner surface 14 which defines a chamber 16 of generally circular cross-section. The chamber 16 is located in a proximal section of the catheter hub 12. In a distal region of the chamber 16 the inner surface 14 of the catheter hub is provided with an annular retaining depression 18 the function of which will be discussed in more detail further below.

The needle 20 having distal and proximal ends extends through the chamber 16 of the catheter hub 12 as well as through the catheter tube 10. The needle 20 comprises a needle shaft 22 and a needle tip 24 at its distal end. A needle hub 26 is attached to the proximal end of the needle 20. The needle 20 defines said axial (longitudinal) direction A and the needle shaft 22 has a generally constant principal profile, except for an enlargement of the radial dimension of the needle 20 in at least one direction as compared to the principal profile, which is positioned in the region of the needle tip 24 and forms an engagement means (not shown). Preferably, the engagement means is made by crimping of the needle 20. However, it could also be made by welding, milling, cold heading or expanding of the needle. The function of the engagement means will be discussed in more detail further below.

FIG. 1 shows the intravenous catheter apparatus in a condition prior to use, in which the needle 20 extends all the way through the chamber 16 of the catheter hub 12 as well as the catheter tube 10 and the needle tip 24 protrudes from a distal end of the catheter tube 10. This position of the needle 20 is also referred to as the ready position in this context. It is to be noted that the needle 20 is fixed in its ready position by the needle hub 26 engaging with the catheter hub 12.

In order to prevent accidental pricking by the needle 20 prior to use of the intravenous catheter apparatus, a tubular cover 30 covers the catheter tube 10 and the portion of the needle 20 extending therethrough. A proximal end portion of the cover 30 is removably fixed to a distal end portion of the catheter hub 12.

The intravenous catheter apparatus further comprises a needle guard 32 for protecting the needle tip 24 after use of the needle 20, i.e. after placement of the catheter tube 10 in and withdrawal of the needle 20 from a patient's vein. The needle guard 32 is slidably arranged on the needle shaft 22 and received in the chamber 16.

As can be seen in more detail in FIGS. 2 to 5, the needle guard 32 comprises a tubular base portion 34 and first and second arms 36, 38 extending from a distal side of the tubular base portion 34 generally in the axial direction. The base portion 34 and the arms 36, 38 are integrally made of a plastic material, for example by injection molding.

The base portion 34 has an axial through-bore 40 for receiving the needle 20. The through-bore 40 comprises first and second sections 42, 44 both having cross-sections that are larger than the principal profile of the needle 20, the cross-section of the second section 44 being even larger than the cross-section of the first section 42.

A stopping element 46 in the shape of a disk-like plate, such as a washer, is arranged at the distal side of the base portion 34, for example by insert molding. The stopping element 46 is made of a material different from the material of the base portion 34, for example of a metal material. The stopping element 46 has an axial bore 48 which is aligned with the through-bore 40 of the base portion 34 and which has a cross-section which is smaller than that of the through-bore 40 of the base portion 34. More specifically, the cross-section of the axial bore 48 of the stopping element 46 is adapted to the principal profile of the needle 20 such that the stopping element 46 can slide along the needle shaft 22 with minimum friction. However, a maximum dimension of the axial bore 48 transverse to the longitudinal direction A is smaller than a maximum dimension of the engagement means provided on the needle 20 transverse to the longitudinal direction so as to prevent the engagement means from passing through the stopping element 46 and, thus, to prevent the needle guard 32 from sliding off the needle 20.

Figure 2:
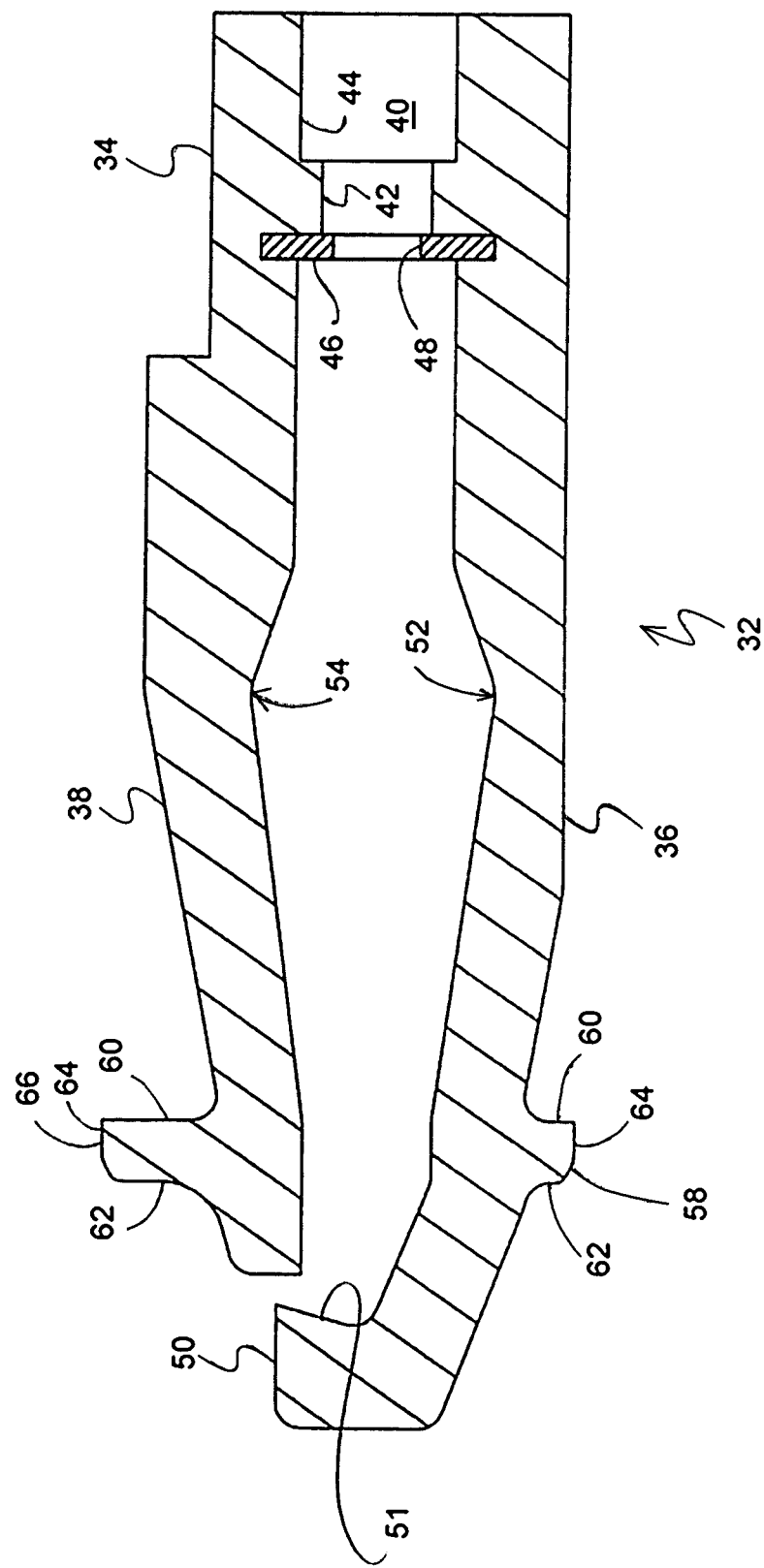
FIG. 2 is a longitudinal sectional view of a needle guard of the intravenous catheter apparatus of FIG. 1 without a tension element.
Figure 3:
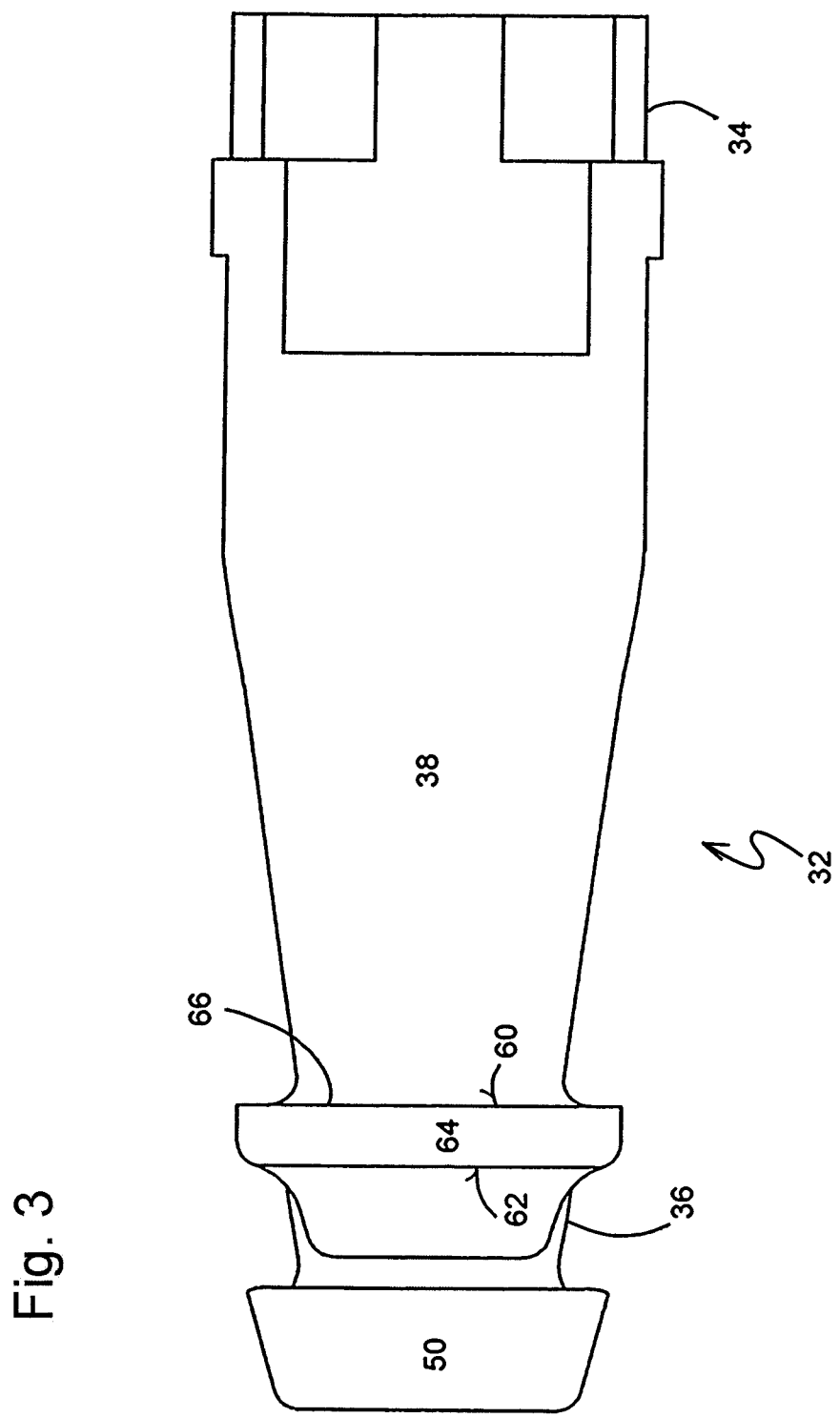
FIG. 3 is a top view of the needle guard of FIG. 2.
Figure 4:
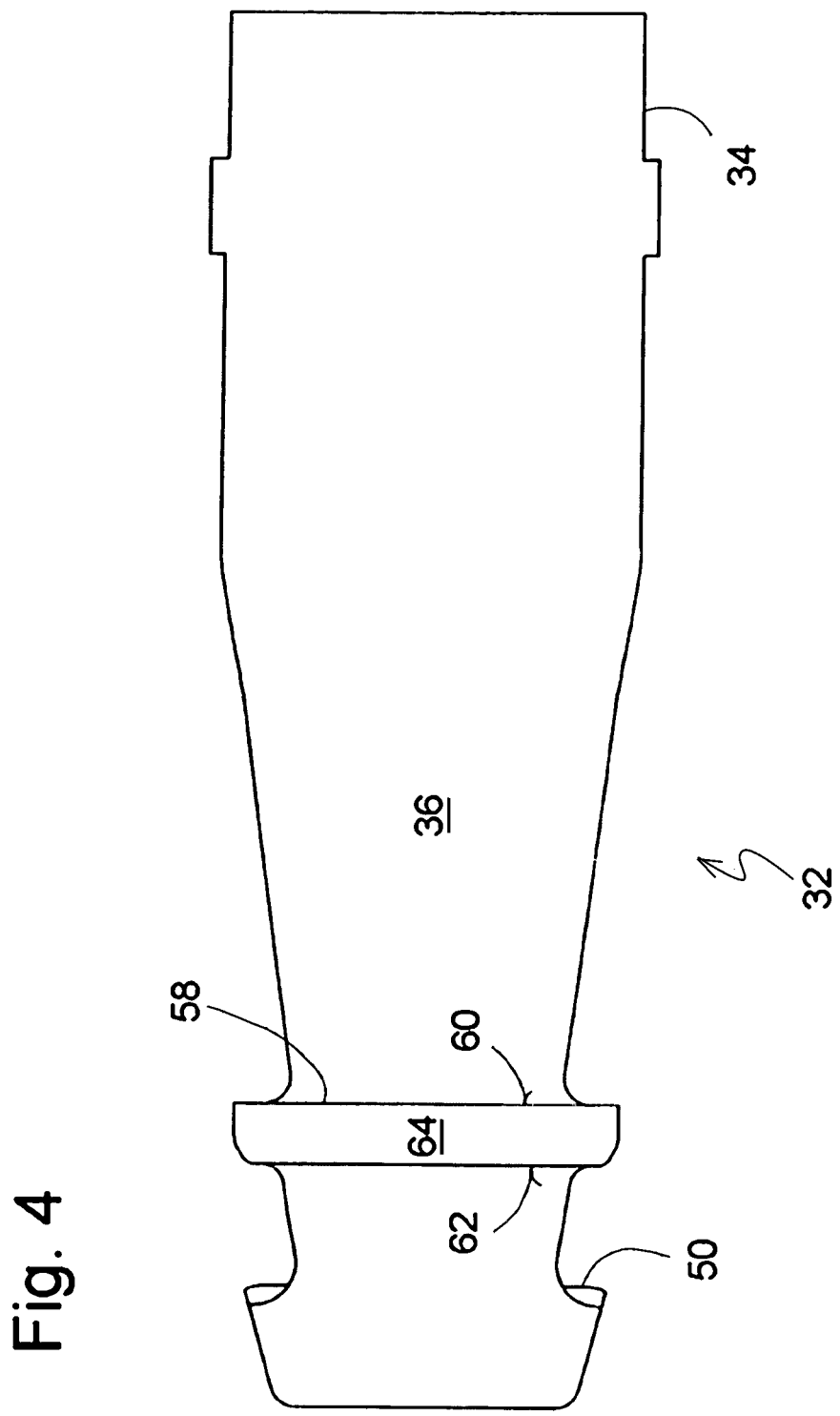
FIG. 4 is a bottom view of the needle guard of FIG. 2.
Figure 5:
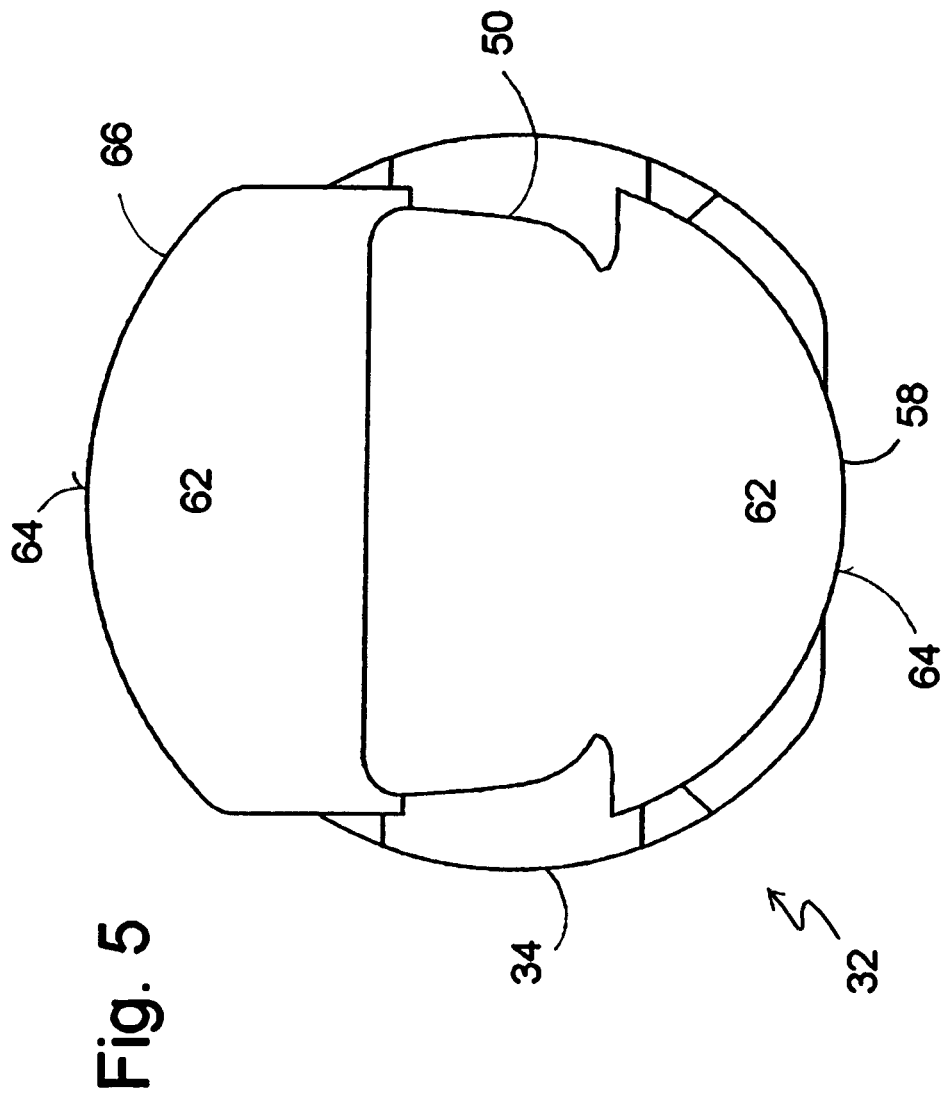
FIG. 5 is a front view of a distal end of the needle guard of FIG. 2.

The first arm 36 of the needle guard 32 is longer than the second arm 38 and has a massive distal end section 50 having an undercut 51 for catching the needle tip 24. The distal end section 50 is angled towards the second arm 38 and overlaps with the second arm 38 (FIG. 2). In its ready position the needle 20 extends completely through the needle guard 32 (FIG. 1). In this situation the distal end section 50 of the first arm 38 is supported on the needle shaft 22 thereby deflecting the first arm 36 radially outwards. In order to facilitate deflection of the first arm 36, the first arm 36 has a narrowed portion 52 of reduced cross-section approximately in a middle region of the arm 36. In contrast to the first arm 36 and because of a lack of angled distal end section, the second arm 38 is not significantly deflected by the needle 20 extending through the needle guard 32. Nonetheless, the second arm 38 has a similar narrowed portion 54 the reason for which will become apparent further below.

Even though the first and second arms 36, 38 have certain elastic properties, a tension element, for example a rubber band 56, surrounds a distal section of the arms 36, 38 such that deflection of the first arm 36 occurs mainly against a restoring force of the tension element (FIG. 1).

When the needle 20 is withdrawn from the catheter tube 10 after placement of the catheter tube 10 in a patient's vein, the needle 20 slides though the needle guard 32 until the needle tip 24 passes the angled distal end section 50 of the first arm 36. At this point the angled distal end section 50 is no longer supported on the needle shaft 22 and the first arm 36—mainly by force of the rubber band 56—snaps back into its relaxed state with the angled distal end section 50 now blocking the needle tip 24. It will be appreciated that the length of the first arm 36 and the distance of the engagement means from the needle tip 24 are adapted to each other such that the needle tip 24 received in the needle guard 32 has a minimum of clearance with respect to axial movement in the needle guard 32.

In order to prevent the needle guard 32 from being prematurely removed from the chamber 16 of the catheter hub 12, i.e. before the needle tip 24 is covered by the needle guard 32, the first arm 36 is provided with a disc-like first retaining protrusion 58 engaging with the retaining depression 18 in the inner surface 14 of the catheter hub 14 in the deflected state of the first arm 36. The first retaining protrusion 58 has generally flat proximal and distal faces 60, 62 and a convex, in particular part-cylindrical, peripheral surface 64 the radius of which is adapted to the radius of the inner surface 14 of the catheter hub 12 in the region of the retaining depression 18. The height of the first retaining protrusion 58, i.e. its dimension seen in the radial direction, is adapted such that the first retaining protrusion 58 disengages from the retaining depression 18 when the first arm 36 snaps back into its relaxed state.

The second arm 38 is provided with a disc-like second retaining protrusion 66 which is similar to the first retaining protrusion 58 and which extends in a radial direction opposite from the first retaining protrusion 58. The second retaining protrusion 66 also has generally parallel proximal and distal faces 60, 62 as well as a convex, in particular part-cylindrical, peripheral surface 64. The height of the second retaining protrusion 66, i.e. its dimension seen in the radial direction, is adapted such that the retaining protrusion 66 engages with the retaining depression 18 when the needle 20 is in its ready position. In order to disengage the retaining protrusion 66 from the retaining depression 18, the second arm 38 can be deflected slightly radially inwards towards the needle 20 when the pulling force on the needle 20 becomes great enough.

As can be seen from FIG. 1, the axial dimension, i.e. width, of the retaining depression 18 is significantly larger than the axial dimension, i.e. width, of the retaining protrusions 58, 66. For example, the width of the retaining depression 18 can be three to five times the width of the retaining protrusions 58, 66, although other ratios are possible as long as reliable engagement between the retaining depression 18 and the retaining protrusions 58, 66 is ensured.

REFERENCE NUMERALS 10 catheter tube
12 catheter hub
14 inner surface
16 chamber
18 retaining depression
20 needle
22 needle shaft
24 needle tip
26 needle hub
30 tubular cover
32 needle guard
34 base portion
36 first arm
38 second arm
40 through-bore
42 first section
44 second section
46 stopping element
48 axial bore
50 distal end section
51 undercut
52 narrowed portion
54 narrowed portion
56 rubber band
58 retaining protrusion
60 proximal face
62 distal face
64 peripheral surface
66 retaining protrusion
A longitudinal direction

What is claimed is:

1. An intravenous catheter assembly, comprising:
an elongated catheter tube having a proximal end and an oppositely disposed distal end;
a catheter hub chamber disposed in the elongated catheter tube and positioned at the proximal end;
an elongated needle having a tipped distal end and slidably disposed in the elongated catheter tube and defining an axial direction;
a needle guard slidably connected to the needle, and further comprising:
  a base portion;
  a first arm extending from the base portion, having a narrowed portion for facilitating deflection of the first arm, and terminating in an undercut distal end portion for catching the tipped distal end when the needle is in a used position;
  a second arm extending from the base portion and disposed opposite the first arm; and
  a metallic stopping member for engaging the needle to prevent proximal motion while allowing distal motion when the needle extends between the first arm and the second arm;
wherein the undercut distal end portion overlaps with the second arm;
a retainer for holding the needle guard in the catheter hub chamber when the first arm is outwardly deflected, the retainer including an annular depression formed in the catheter hub chamber and a first retaining protrusion extending from the first arm and matingly engageable with the annular depression to resist premature removal of the needle guard from the catheter hub chamber, and a second retaining protrusion extending from the second arm and matingly engageable with the annular depression when the needle is in a ready position;
wherein the needle extends through the catheter hub chamber when occupying the ready position;
wherein the metallic stopping member is received in the catheter hub chamber when the needle occupies the ready position;

wherein the first arm is deflected radially outward against an oppositely directed restoring force from the needle when the needle is in the ready position;

wherein the tipped distal end engages the undercut distal portion when the tipped distal end is withdrawn into the needle guard;

wherein the metallic stopping member prevents the needle guard from sliding off the needle;

wherein the first arm is longer than the second arm.

2. The intravenous catheter assembly claim 1 wherein when the first arm is outwardly deflected, the second arm remains substantially undeflected.

3. The intravenous catheter assembly of claim 1 and further comprising a tension element connected to the first arm to provide the restoring force when the first arm is outwardly deflected.

4. The intravenous catheter assembly of claim 1 wherein withdrawal of the needle from the ready position moves the tipped needle end into the needle guard and engages the tipped distal end with the undercut distal portion.

5. The intravenous catheter assembly of claim 1 wherein the first retaining protrusion is dimensioned such that the first retaining protrusion disengages the annular depression when the first arm becomes undeflected.

6. The intravenous catheter assembly of claim 5 wherein the needle exits the ready position a pulling force is generated on the second arm to yield sufficient deflection to disengage the second retaining protrusion from the annular depression.

7. An intravenous catheter assembly, comprising:
a catheter hub chamber;
a needle having a tipped distal end;
a plastic needle guard slidably connected to the needle, and further comprising:
  a base portion;
  a first arm extending from the base portion having an undercut distal end portion for engaging the needle when the needle is in a used position;
  a second arm extending from the base portion and disposed generally parallel with the first arm, and
  a metallic needle-engaging stopping member having a disk-like shape of a material that is different from the base portion to allow only distal motion when the needle extends between the first arm and the second arm; and
a retainer for holding the needle guard in the catheter hub chamber when the first arm is deflected, the retainer including an annular depression formed in the catheter hub chamber and a first retaining protrusion extending from the first arm and matingly engageable with the annular depression to resist premature removal of the needle guard from the catheter hub chamber and a second retaining protrusion extending from the second arm and matingly engageable with the annular depression when the needle is in a ready position;

wherein the needle extends through the catheter hub chamber when occupying the ready position;

wherein the metallic stopping member is received in the catheter hub chamber when the needle occupies the ready position;

wherein the first arm is deflected radially outward from the needle against an oppositely directed restoring force when the needle is in the ready position;

wherein the oppositely directed restoring force is generated by one of the group comprising certain elastic properties of the first arm, a tensioning member acting upon the first arm, and combinations thereof; and wherein the metallic stopping member prevents the needle guard from sliding off the needle.

8. The intravenous catheter assembly of claim 7 wherein the first retaining protrusion is dimensioned such that the first retaining protrusion disengages the annular depression when the first arm becomes undeflected.

9. The intravenous catheter assembly of claim 7 wherein the needle exits the ready position a pulling force is generated on the second arm to yield sufficient deflection to disengage the second retaining protrusion from the annular depression.

* * * * *